US00PP28863P3

(12) United States Plant Patent
Snijder

(10) Patent No.: US PP28,863 P3
(45) Date of Patent: Jan. 9, 2018

(54) POINSETTIA PLANT NAMED 'EURZ0002'

(50) Latin Name: *Euphorbia pulcherrima*
Varietal Denomination: EURZ0002

(71) Applicant: SYNGENTA PARTICIPATIONS AG, Basel (CH)

(72) Inventor: Ronald Snijder, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 72 days.

(21) Appl. No.: 14/545,676

(22) Filed: Jun. 5, 2015

(65) Prior Publication Data

US 2016/0007517 P1 Jan. 7, 2016

(30) Foreign Application Priority Data

Jul. 2, 2014 (CA) ..... PBR 14-8382
Feb. 2, 2015 (QZ) ..... PBR 2015/0272

(51) Int. Cl.
*A01H 5/02* (2006.01)

(52) U.S. Cl.
USPC ..... Plt./304

(58) Field of Classification Search
USPC ..... Plt./263.1, 302, 303, 304
See application file for complete search history.

(56) References Cited

U.S. PATENT DOCUMENTS

PP13,618 P2 * 3/2003 Dummen ..... A01H 5/00 Plt./304
PP22,035 P2 * 7/2011 Zerr ..... A01H 5/00 Plt./307

OTHER PUBLICATIONS

Broertjes et al. 1978. Application of Mutation Breeding Methods in the improvement of Vegetatively Propagated Crops. Elsevier Scientific Publishing Company pp. 118-119.*
Pot Plants 2015 Catalog. FloriPro Services; Syngenta. http://www.blondyromania.ro/pdf/BlondyRomania_Catalog_Cyclamen_Poinsettia_Crizanteme_2015.pdf. 8 pages.*

* cited by examiner

*Primary Examiner* — Susan McCormick Ewoldt
*Assistant Examiner* — Karen Redden
(74) *Attorney, Agent, or Firm* — Dale Skalla

(57) ABSTRACT

A new Poinsettia plant named 'EURZ0002' particularly distinguished by cream-white flower color, relatively large inflorescences with the bracts a little upright directed, early flowering response, dark green foliage, ovate leaves, and medium to strong vigour with good branching.

1 Drawing Sheet

Latin name of the genus and species of the plant claimed: *Euphorbia pulcherrima.*

Varietal denomination: 'EURZ0002'.

BACKGROUND OF THE NEW PLANT

The present invention comprises a new Poinsettia, botanically known as *Euphorbia pulcherrima*, and hereinafter referred to by the variety name 'EURZ0002'.

'EURZ0002' is a product of a planned breeding program. The new cultivar has cream-white bracts color, relatively large inflorescences with the bracts a little upright directed, early flowering response, dark green foliage, ovate leaves, and medium to strong vigour with good branching.

'EURZ0002' originates from an induced mutation and was selected in Enkhuizen, Netherlands among greenhouse plants of the parent variety.

The parent was the commercial plant designated 'SYEP22432', U.S. Plant Pat. No. 22,035, also known as 'Titan Red', with bright red bract color, early flowering response, dark green leaves, upright and a little more vigorously growing than 'EURZ0002'.

Young plants of the parent variety had been exposed to x-ray radiation in Enkhuizen, Netherlands. The treated plants were then grown out in a greenhouse Enkhuizen, Netherlands.

During the flowering season from November to December 2011, 'EURZ0002' was discovered and selected as a single mutated plant. The first asexual propagation was made a few months later, by taking shoot tip cuttings from the mutated plant. The rooted cuttings were grown out and used for the first flowering trial in Enkhuizen, Netherlands in the fall of 2012.

Since then, the clone has been repeatedly asexually reproduced by cuttings in Enkhuizen, Netherlands and found to be true to type, uniform and stable for the new characteristic.

BRIEF SUMMARY OF INVENTION

Horticultural examination of plants grown from cuttings of the plant initiated in the summer of 2012, and continuing thereafter, has demonstrated that the combination of characteristics as herein disclosed for 'EURZ0002' are firmly fixed and are retained through successive generations of asexual reproduction.

'EURZ0002' has not been observed under all possible environmental conditions. The phenotype may vary significantly with variations in environment such as temperature, light intensity and day length.

Plant Breeder's Rights for this cultivar were applied for in Canada on Jul. 2, 2014 No. 14-8382; and in the European Union (CPVO) on Feb. 2, 2015, No. 2015/0272.

The following traits have been repeatedly observed and are determined to be basic characteristics of the new variety. The combination of these characteristics distinguishes this Poinsettia as a new and distinct variety.

BRIEF DESCRIPTION OF THE PHOTOGRAPHS

Figure 1:
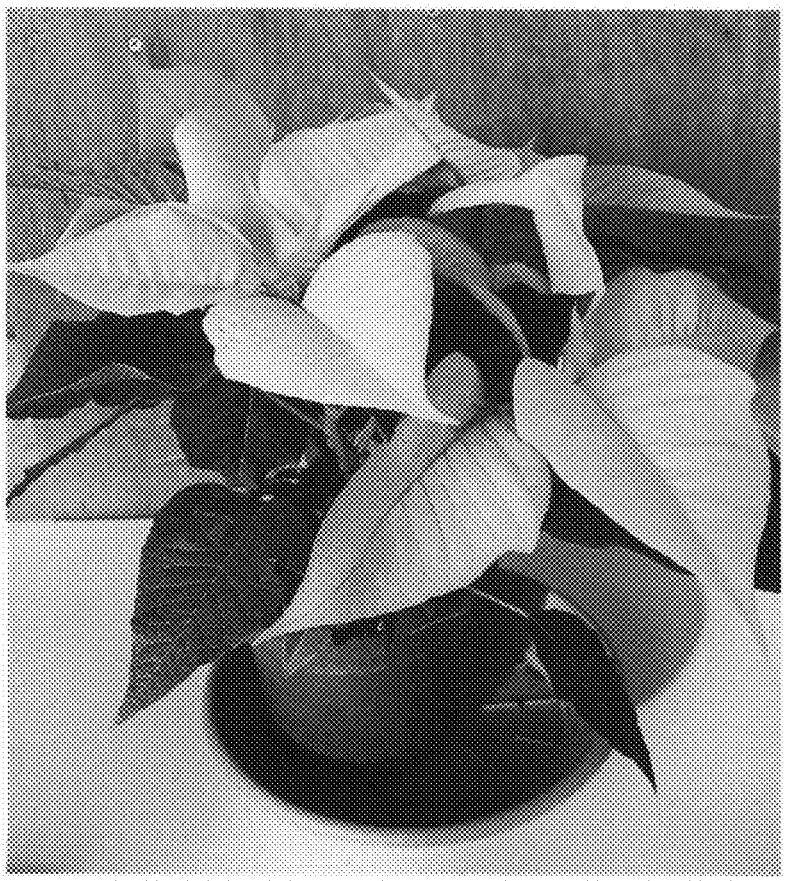
Figure 2:
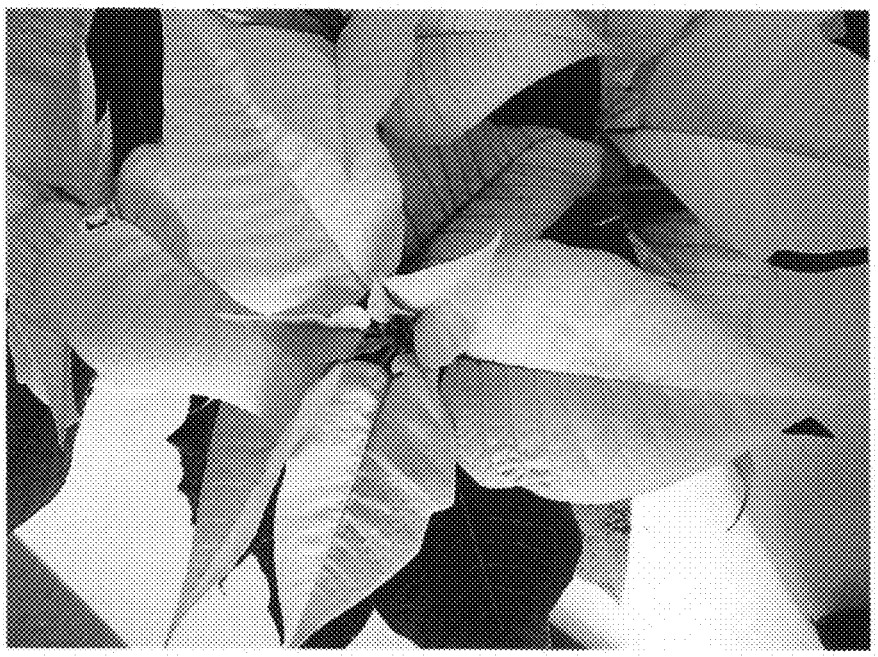

The accompanying photographic drawing shows typical flower and foliage characteristics of 'EURZ0002' with colors being as true as possible with an illustration of this type. The photographic drawings show flowering potted plants of the new variety. FIG. 1 is a close view flower bracts, and FIG. 2, taken shows a small flowering plant.

DETAILED BOTANICAL DESCRIPTION

The measurements were taken in Hauwert, Netherlands in mid-November 2014 on about 20 week old plants growing in a greenhouse. Cultivation of these plants had started in late July 2014 with planting of rooted cuttings into 12 cm pots and terminal pinching about 2 weeks later. The plants were grown under natural day light in the fall (no black cloth to initiate earlier flowering) and at the moderately warm temperature of 18° C. for the bench heating.

The aforementioned photographs were both taken during the flowering season in mid-December 2012 in a greenhouse in Enkhuizen, Netherlands. The plants were about 20 weeks old and grown in 12 cm pots.

Color references are made to The Royal Horticultural Society Colour Chart (R.H.S.) 2001.

TABLE 1

DIFFERENCES BETWEEN THE NEW VARIETY 'EURZ0002' AND A SIMILAR VARIETY

| | 'EURZ0002' | 'FISMIRWHI', commercially 'Mira White', U.S. Plant Pat. No. 20,958 |
|---|---|---|
| Leaves length: | 6.5 cm | 4.5-7 cm |
| Bract shape: | Ovate, with very shallow lobes | Deep lobes, strong lobing |
| Plant habit: | more open | Tighter, more compact |
| Cyathia: | Smaller | Bigger |

Plant:

*Form, growth and habit.*—Shrub, with the branches slanting upright, good branching.

*Plant height (inflorescence included).*—20 cm.

*Plant width.*—35 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155B but whiter.

Foliage:

*Arrangement.*—Alternate, 6-8 leaves per branch.

*Immature, leaf color, upper surface.*—Approximately RHS 147A.

*Immature, leaf color, lower surface.*—RHS 137A.

*Mature, leaf color, upper surface.*—RHS 147A.

*Mature, leaf color, lower surface.*—RHS 137A.

*Length.*—10-13 cm.

*Width.*—8 cm.

*Shape.*—Ovate, with 2 to 4 lobes.

*Base shape.*—Truncate to rounded.

*Apex shape.*—Acuminate.

*Margin.*—Entire; lobes, when present mostly rounded.

*Aspect.*—Leaf blades are horizontally or slightly downwards directed.

*Texture, upper surface.*—Smooth.

*Texture, lower surface.*—Smooth, apart from the protruding veins.

*Color of veins, upper surface.*—RHS 147C.

*Color of veins, lower surface.*—RHS 144B.

*Petiole color, upper surface.*—RHS 144B.

*Lower surface.*—RHS 145B.

*Length.*—Most often 5-7 cm.

*Diameter.*—0.2-0.3 cm.

*Aspect.*—Slightly upward directed.

*Texture.*—Glabrous.

Stem:

*Quantity of main branches per plant.*—About 3-4.

*Color of stem.*—Mainly RHS 143C-144B at the upper third of the stems.

*Length of stem.*—17 cm.

*Diameter.*—0.6-0.8 cm.

*Length of internodes.*—2 cm.

*Texture.*—Glabrous.

*Color of peduncle.*—RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, botanically (opening of the stamen, shedding of pollen).*—Around December 1.

*Flowering, commercially (sufficiently colored bracts).*—Mid-November.

*Flowering response time.*—About 6.5 weeks from equinox.

*Duration of flowering.*—Depends on light and environment, at least 4-6 weeks of 'shelf' life.

*Fragrance.*—Absent.

*Shape of inflorescence.*—Rosette-like whorl, star-shaped; bracts borne nearly horizontally to downwards directed.

*Diameter of inflorescence.*—25-27 cm.

*Inflorescence, vertical diameter.*—5 cm.

*Number of completely colored bracts per inflorescence (sized over 2 cm).*—12-14.

*Single bract, shape.*—Ovate with relatively long, pointed tips, without or with weak lobes.

*Bract, apex.*—Acuminate.

*Bract, base.*—Rounded.

*Single bract, length of blade.*—13-14 cm, younger bracts diminishing in size.

*Single bract, width of blade.*—9 cm.

*Bract color, upper side.*—Close to RHS 2D.

*Bract color, lower side.*—RHS 150D.

*Vein color, upper surface.*—RHS 154C.

*Vein color, lower surface.*—RHS 151D.

*Texture.*—Weakly rugose, glabrous.

*Bract petiole color, upper surface.*—RHS 144B.

*Bract petiole color, lower surface.*—RHS 144C.

*Bract petiole, length.*—About 2.5-3.5 cm, shorter with younger bracts.

*Bract petiole diameter.*—0.2-0.3 cm.

Cyme (true inflorescence):

*Cyme, diameter.*—1.5 cm.

*Number of cyathia.*—5-7, borne in a tight cluster.

*Cyathium, shape.*—Ovate.

*Cyathium, diameter.*—0.3-0.4 cm.

*Cyathium, length.*—0.6-0.7 cm.

*Color.*—RHS 144C.

*Nectar cups.*—Usually one per cyathium.

*Nectar cup, width.*—0.2-0.4 cm.

*Nectar cup, color.*—RHS N144B.

Reproductive organs:

*Stamen* (*actually reduced male florets*).—Usually in a small bunch of 10-20 at the top of the cyathium.

*Shape.*—Strap-like.

*Filament length.*—0.2 cm.

*Filament color.*—RHS 1A.

*Anther color.*—RHS 11A.

*Anther diameter.*—0.1 cm.

*Pollen quantity.*—Moderate (normal quantity).

*Pollen color.*—RHS 12A.

*Female flowers.*—Not observed; May appear sparse in mid-winter, as occurrence depends much on light intensity, appear (if at all) about 4 weeks later than the stamen, a single flower emerges from the top of the cyathium with a short pedicel.

*Fertility/seed set.*—Has not been observed on this plant.

Disease/pest resistance: Disease/pest resistance has not been observed on this plant.

What is claimed is:

1. A new and distinct variety of Poinsettia plant named 'EURZ0002', substantially as illustrated and described herein.

* * * * *